United States Patent
Xu et al.

(10) Patent No.: US 12,285,560 B2
(45) Date of Patent: Apr. 29, 2025

(54) VENTILATION DETECTION METHOD AND DEVICE, VENTILATION APPARATUS

(71) Applicants: SHENZHEN MINDRAY BIO-MEDICAL ELECTRONICS CO., LTD., Shenzhen (CN); Peking Union Medical College Hospital, Chinese Academy of Medical Science and Peking Union Medical College, Beijing (CN)

(72) Inventors: Jun Xu, Beijing (CN); Jinglei Liu, Shenzhen (CN); Xuezhong Yu, Beijing (CN); Yangyang Fu, Beijing (CN); Xinru Zou, Shenzhen (CN); Xiaoyong Zhou, Shenzhen (CN)

(73) Assignees: SHENZHEN MINDRAY BIO-MEDICAL ELECTRONICS CO., LTD., Shenzhen (CN); PEKING UNION MEDICAL COLLEGE HOSPITAL, CHINESE ACADEMY OF MEDICAL SCIENCE AND PEKING UNIONMEDICAL COLLEGE, Beijing (CN)

( * ) Notice: Subject to any disclaimer, the term of this patent is extended or adjusted under 35 U.S.C. 154(b) by 1119 days.

(21) Appl. No.: 17/169,523

(22) Filed: Feb. 7, 2021

(65) Prior Publication Data

US 2021/0154421 A1 May 27, 2021

Related U.S. Application Data

(63) Continuation of application No. PCT/CN2018/101599, filed on Aug. 21, 2018.

(51) Int. Cl.
*A61M 16/00* (2006.01)

(52) U.S. Cl.
CPC .... *A61M 16/0003* (2014.02); *A61M 16/0051* (2013.01); *A61M 2016/0027* (2013.01);
(Continued)

(58) Field of Classification Search
CPC .... A61M 16/00–0003; A61M 16/0051; A61M 16/021–026; A61M 2016/0015–0042
See application file for complete search history.

(56) References Cited

U.S. PATENT DOCUMENTS

| 6,532,960 B1 * | 3/2003 | Yurko | A61M 16/024 |
| | | | 128/204.26 |
| 2009/0221926 A1 | 9/2009 | Younes et al. | |

(Continued)

FOREIGN PATENT DOCUMENTS

| CN | 103169476 A | 6/2013 |
| CN | 103180002 A | 6/2013 |

(Continued)

OTHER PUBLICATIONS

First Office Action issued in related Chinese Application No. 201880094803.4, mailed Mar. 28, 2022, 54 pages.
(Continued)

*Primary Examiner* — Rachel T Sippel
(74) *Attorney, Agent, or Firm* — BAYES PLLC

(57) ABSTRACT

A ventilation detection method applied to a ventilation apparatus. The method may include monitoring respiratory parameters during mechanical ventilation of a patient by using a ventilation apparatus, the respiratory parameters at least comprising one of airway pressure and airway flow, and using changes in the respiratory parameters to identify whether man-machine counteraction or ventilation leakage has occurred.

19 Claims, 7 Drawing Sheets

(52) U.S. Cl.
CPC . *A61M 2016/0036* (2013.01); *A61M 2205/15* (2013.01); *A61M 2205/3334* (2013.01); *A61M 2205/502* (2013.01)

(56) References Cited

U.S. PATENT DOCUMENTS

| | | | |
|---|---|---|---|
| 2012/0073574 A1 | 3/2012 | Gutierrez | |
| 2014/0034054 A1 | 2/2014 | Angelico et al. | |
| 2015/0107584 A1 | 4/2015 | Jafari et al. | |
| 2021/0205558 A1* | 7/2021 | Vicario | A61M 16/0057 |

FOREIGN PATENT DOCUMENTS

| | | |
|---|---|---|
| CN | 103330979 A | 10/2013 |
| CN | 103977492 A | 8/2014 |
| CN | 106029141 A | 10/2016 |
| EP | 3308819 A1 | 4/2018 |
| WO | 2010097717 A1 | 9/2010 |
| WO | 2015104669 A1 | 7/2015 |
| WO | 2017029629 A1 | 2/2017 |
| WO | 2017068464 A1 | 4/2017 |
| WO | 2017140500 A1 | 8/2017 |

OTHER PUBLICATIONS

Shenyang Yu, "Clinical Practice of Mechanical Ventilation", People's military medical press, Sep. 30, 2008, pp. 87-89, 144-155, 516-527, 869.

Extended European Search Report issued in related European Application No. 18931156.6, mailed Jul. 22, 2021, 12 pages.

International Search Report issued in corresponding International Application No. PCT/CN2018/101599, mailed Mar. 6, 2019, 4 pages.

* cited by examiner

VENTILATION DETECTION METHOD AND DEVICE, VENTILATION APPARATUS

CROSS-REFERENCE TO RELATED APPLICATIONS

This application is a continuation of PCT Application NO. PCT/CN2018/101599, filed Aug. 21, 2018, entitled "VENTILATION DETECTION METHOD AND DEVICE, VENTILATION APPARATUS, AND STORAGE MEDIUM," the entire contents of which are incorporated herein by reference.

TECHNICAL FIELD

Embodiments of the disclosure relate to the technical field of medical instruments, and in particular to a ventilation detection method and device, a ventilation apparatus, and a storage medium.

BACKGROUND

A ventilation apparatus, such as a ventilator, is a medical apparatus that can replace and improve spontaneous ventilation, have been widely used in the treatment of a patient with respiratory insufficiency, respiratory failure, etc. caused by various reasons, which is very important for saving and prolonging the patient's life.

During the mechanical ventilation by using a ventilator, the ventilation setup of the ventilator directly influences the ventilation effect of the patient. If the ventilation setup of the ventilator meets the patient's needs, the ventilator can work well in the recovery and treatment of the patient. However, if the ventilation setup of the ventilator does not meet the patient's needs, a man-machine counteraction event often has occurred, that is, the patient's breathing is not synchronized with the ventilator, thereby affecting the therapeutic effect.

SUMMARY

In order to solve the above technical problems, an embodiment of the disclosure expects to provide a ventilation detection method and device, a ventilation apparatus, and a storage medium so as to, during mechanical ventilation of a patient, identify man-machine counteraction or ventilation leakage according to specific changes in respiratory parameters and adjust the ventilation parameters or make a prompt according to the identified event to meet the patient's ventilation needs, thereby improving the therapeutic effect.

The technical solution of the embodiment of the disclosure can be implemented as follows:

the embodiment of the disclosure provides a ventilation detection method applied to a ventilation apparatus, the method may include:
  monitoring respiratory parameters during mechanical ventilation of a patient by using a ventilation apparatus, the respiratory parameters may at least include one of airway pressure and airway flow; and
  using changes in the respiratory parameters to identify whether man-machine counteraction or ventilation leakage has occurred.

In the above solution, the step of using changes in the respiratory parameters to identify whether man-machine counteraction or ventilation leakage has occurred may include:

analyzing a change trend of the respiratory parameter; and
identifying whether man-machine counteraction or ventilation leakage has occurred according to the change trend of the respiratory parameter.

In the above solution, after identifying that man-machine counteraction has occurred according to the change trend of the respiratory parameter, the method may further include:
  identifying the type of man-machine counteraction according to the change trend of the respiratory parameter.

In the above solution, the type of man-machine counteraction may include one or more of improper setup of inspiratory flow, improper setup of inspiratory pressure rise time, improper setup of inspiratory duration, and improper setup of expiratory duration.

In the above solution, the step of identifying the improper setup of inspiratory flow according to the change trend of the respiratory parameter specifically may include:
  in a constant-flow ventilation mode, when pressure drop has occurred in a gas delivery section in an inspiration stage, determining that the inspiratory flow of the ventilation apparatus may be set insufficient.

In the above solution, the step of identifying the improper setup of inspiratory pressure rise time according to the change trend of the respiratory parameter specifically may include:
  in a pressure ventilation mode, when the airway pressure is greater than a target value at the end of an inspiratory pressure rise stage and the airway pressure fluctuates, determining that the inspiratory pressure rise time of the ventilation apparatus may be set too short; and/or
  in the pressure ventilation mode, when the airway pressure has a pressure drop in the inspiratory pressure rise stage, determining that the inspiratory pressure rise time of the ventilation apparatus may be set too long.

In the above solution, the step of identifying the improper setup of inspiratory duration according to the change trend of the respiratory parameter specifically may include:
  when the airway pressure has a rise or the airway flow has an accelerated drop in an inspiration-to-expiration stage, determining that the inspiratory duration of the ventilation apparatus may be set too long; and
  when the airway pressure has a non-monotonic drop and/or the airway flow has a non-monotonic rise in an expiration stage, determining that the inspiratory duration of the ventilation apparatus may be set too short.

In the above solution, the step of identifying the improper setup of expiratory duration according to the change trend of the respiratory parameter specifically may include:
  calculating the change in volume according to the airway flow; and
  when the airway flow is incapable of returning to a baseline but the volume is capable of returning to the baseline in an end expiration stage, determining that the expiratory duration of the ventilation apparatus may be set too short.

In the above solution, the step of identifying the ventilation leakage according to the change trend of the respiratory parameter specifically may include:
  calculating the change in volume according to the airway flow; and
  when the airway flow is incapable of returning to the baseline and the volume is incapable of returning to the baseline in the end expiration stage, determining that the ventilation apparatus may have a ventilation leakage.

In the above solution, after the step of identifying the type of man-machine counteraction according to the change trend of the respiratory parameter, the method further may include:

outputting ventilation setup adjustment information of the ventilation apparatus according to the identified type of man-machine counteraction.

In the above solution, after the step of identifying the type of man-machine counteraction according to the change trend of the respiratory parameter, the method further may include:

adjusting the ventilation parameter of the ventilation apparatus according to the identified type of man-machine counteraction.

The embodiment of the disclosure may provide a ventilation detection device applied to a ventilation apparatus, the device may include:

an acquisition unit may be configured to monitor respiratory parameters during mechanical ventilation of a patient by using a ventilation apparatus, the respiratory parameters may at least include one of airway pressure and airway flow; and a processing unit may be configured to use changes in the respiratory parameters to identify whether man-machine counteraction or ventilation leakage has occurred.

In the above device, the processing unit may be configured to analyze a change trend of the respiratory parameter; and identifying whether man-machine counteraction or ventilation leakage has occurred according to the change trend of the respiratory parameter.

In the above device, the processing unit may be configured to, after identifying that man-machine counteraction has occurred according to the change trend of the respiratory parameter, identify the type of man-machine counteraction according to the change trend of the respiratory parameter.

In the above device, the type of man-machine counteraction may include one or more of improper setup of inspiratory flow, improper setup of inspiratory pressure rise time, improper setup of inspiratory duration, and improper setup of expiratory duration.

In the above device, the step of identifying the improper setup of inspiratory flow by using the processing unit according to the change trend of the respiratory parameter specifically may include:

in a constant-flow ventilation mode, when pressure drop has occurred in a gas delivery section in an inspiration stage, determining that the inspiratory flow of the ventilation apparatus may be set insufficient.

In the above device, the step of identifying the improper setup of inspiratory pressure rise time by using the processing unit according to the change trend of the respiratory parameter specifically may include:

in a pressure ventilation mode, when the airway pressure is greater than a target value at the end of an inspiratory pressure rise stage and the airway pressure fluctuates, determining that the inspiratory pressure rise time of the ventilation apparatus may be set too short; and/or in the pressure ventilation mode, when the airway pressure has a pressure drop in the inspiratory pressure rise stage, determining that the inspiratory pressure rise time of the ventilation apparatus may be set too long.

In the above device, the step of identifying the improper setup of inspiratory duration by using the processing unit according to the change trend of the respiratory parameter specifically may include:

when the airway pressure has a rise or the airway flow has an accelerated drop in an inspiration-to-expiration stage, determining that the inspiratory duration of the ventilation apparatus may be set too long; and when the airway pressure has a non-monotonic drop and/or the airway flow has a non-monotonic rise in an expiration stage, determining that the inspiratory duration of the ventilation apparatus may be set too short.

In the above device, the step of identifying the improper setup of expiratory duration by using the processing unit according to the change trend of the respiratory parameter specifically may include:

calculating the change in volume according to the airway flow; and when the airway flow is incapable of returning to a baseline and the volume is capable of returning to the baseline in an end expiration stage, determining that the expiratory duration of the ventilation apparatus may be set too short.

In the above device, the step of identifying the ventilation leakage by using the processing unit according to the change trend of the respiratory parameter specifically may include:

calculating the change in volume according to the airway flow; and when the airway flow is incapable of returning to the baseline and the volume is incapable of returning to the baseline in the end expiration stage, determining that the ventilation apparatus may have a ventilation leakage.

In the above device, after the step of identifying the type of man-machine counteraction according to the change trend of the respiratory parameter, the processing unit may output ventilation setup adjustment information of the ventilation apparatus according to the identified type of man-machine counteraction.

In the above device, after the step of identifying the type of man-machine counteraction according to the change trend of the respiratory parameter, the processing unit may adjust the ventilation parameter of the ventilation apparatus according to the identified type of man-machine counteraction.

An embodiment of the disclosure may provide a ventilation apparatus including the above ventilation detection device, the ventilation apparatus including a gas source, an inspiratory branch, an expiratory branch, a display, and a controller, where the gas source may provide gas during mechanical ventilation;

the inspiratory branch may be connected to the gas source, and may provide an inspiratory path during the mechanical ventilation;

the expiratory branch may provide an expiratory path during the mechanical ventilation;

the ventilation detection device may be connected to the inspiratory branch, the expiratory branch, and the controller;

the ventilation detection device may perform ventilation detection during the mechanical ventilation;

the controller may be further connected to the gas source, and control the process of the mechanical ventilation; and the display may be connected to the controller, and display a respiratory waveform during the mechanical ventilation.

The embodiment of the disclosure may provide a computer-readable storage medium, wherein the computer-readable storage medium may store a ventilation detection program, and the ventilation detection program may be executable by a processor to implement the above ventilation detection method.

It can be seen that in the technical solutions of the embodiment of the disclosure, the ventilation detection device may be configured to monitor respiratory parameters during the mechanical ventilation of a patient by using the ventilation apparatus, the respiratory parameters may at least include one of airway pressure and airway flow; and using changes in the respiratory parameters to identify whether man-machine counteraction or ventilation leakage has occurred. That is to say, in the technical solution provided by the embodiment of the disclosure, it is possible to, during mechanical ventilation of a patient, identify man-machine counteraction or ventilation leakage according to specific changes in respiratory parameters and adjust the ventilation parameters or make a prompt according to the identified event to meet the patient's ventilation needs, thereby improving the therapeutic effect.

DESCRIPTION OF THE PREFERRED EMBODIMENTS

In order to understand the features and technical contents of the embodiments of the disclosure in more detail, the implementation of the embodiments of the disclosure will be described in detail with reference to the accompanying drawings, which are for reference only, and are not intended to limit the embodiments of the disclosure.

Embodiment I

Figure 1:
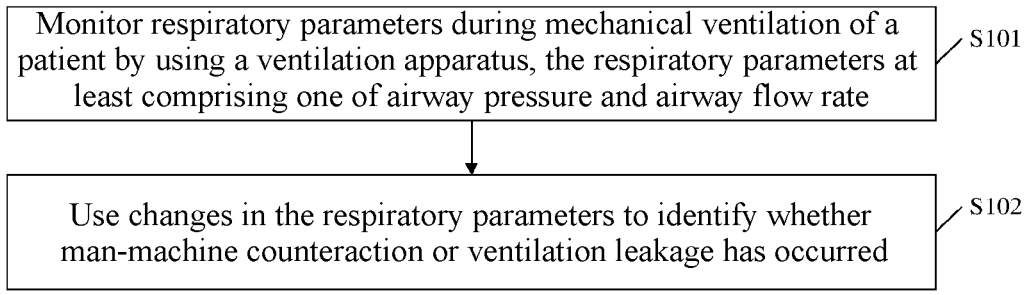
FIG. 1 is a schematic flow chart of a ventilation detection method provided by an embodiment of the disclosure.

The embodiment of the disclosure provides a ventilation detection method applied to a ventilation apparatus. FIG. 1 is schematic flow chart I of a ventilation detection method provided by an embodiment of the disclosure. As shown in FIG. 1, the method mainly may include the following steps:

S101: Respiratory parameters may be monitored during mechanical ventilation of a patient by using a ventilation apparatus, the respiratory parameters may at least include one of airway pressure and airway flow rate.

In the embodiment of the disclosure, the ventilation detection device can monitor respiratory parameters during mechanical ventilation of a patient by using a ventilation apparatus.

It should be noted that, in the embodiment of the disclosure, the respiratory parameters include at least one of airway pressure and airway flow.

It should be noted that, in the embodiment of the disclosure, the ventilation apparatus may be a medical apparatus with a ventilation function, and may be a ventilator or an anesthesia machine. The specific ventilation apparatus may be not limited according to the embodiment of the disclosure.

It should be noted that, in the embodiment of the disclosure, the ventilation detection device may continuously monitor the respiratory parameters, that is, the ventilation apparatus may monitor the respiratory parameters all the time from beginning to end of mechanical ventilation.

It can be understood that during mechanical ventilation of a patient by using the ventilation apparatus, the respiratory parameters may have changes with time. Therefore, in the embodiment of the disclosure, the ventilation detection device may be configured to detect the respiratory parameters, and identify whether man-machine counteraction or ventilation leakage has occurred based on changes in the respiratory parameters and then dealing with it correspondingly.

S102: Changes in the respiratory parameters may be used to identify whether man-machine counteraction or ventilation leakage has occurred.

In the embodiment of the disclosure, after monitoring the respiratory parameters, the ventilation detection device may analyze the change trend of the respiratory parameter, and identify whether man-machine counteraction or ventilation leakage has occurred according to the change trend of the respiratory parameter.

It should be noted that, in the embodiment of the disclosure, after identifying that man-machine counteraction has occurred according to the change trend of the respiratory parameter, the ventilation detection device can further identify the type of man-machine counteraction according to the change trend of the respiratory parameter.

It should be noted that, in the embodiment of the disclosure, the type of man-machine counteraction may include one or more of improper setup of inspiratory flow, improper setup of inspiratory pressure rise time, improper setup of inspiratory duration, and improper setup of expiratory duration.

Specifically, in the embodiment of the disclosure, the step of identifying the improper setup of inspiratory flow by using the ventilation detection device according to the change trend of the respiratory parameter specifically may include: in a constant-flow ventilation mode, when pressure drop has occurred in a gas delivery stage in an inspiration stage, determining that the inspiratory flow of the ventilation apparatus may be set insufficient.

It should be noted that, in the constant-flow ventilation mode, the ventilation apparatus may be preset with gas delivery section and airway flow setup values, and the airway flow of the ventilation apparatus in the gas delivery section of the inspiration stage may be always maintained at the airway flow setup value. Under normal situations, the airway pressure in the gas delivery section of the inspiration stage may have a monotonic rise. However, when the threshold of the airway flow in the gas delivery section does not meet the patient's actual needs, the patient will have strong spontaneous inspiration, which is indicated by the drop of airway pressure in the gas delivery section of the inspiration stage. The specific gas delivery section and airway flow setup values may be not limited in the disclosure.

Figure 2:
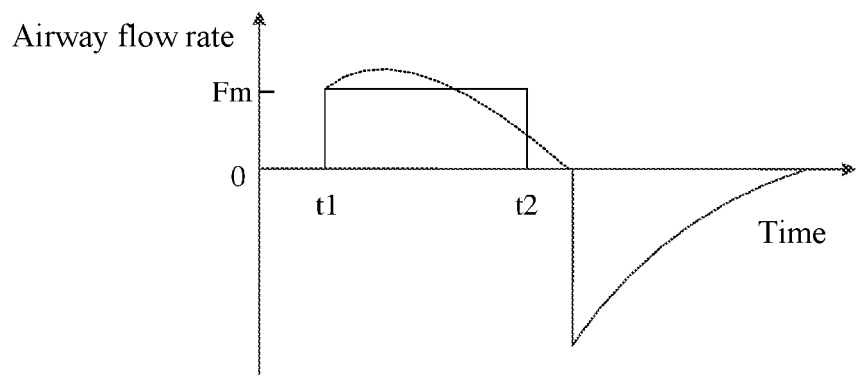
FIG. 2 is an exemplary schematic diagram of waveform of airway flow versus time in a constant-flow ventilation mode provided by an embodiment of the disclosure.

FIG. 2 is an exemplary schematic diagram of waveform of airway flow versus time in a constant-flow ventilation mode provided by an embodiment of the disclosure. As shown in FIG. 2, the gas delivery section of the inspiration stage may be from a time point t1 to a time point t2. The solid line between the time point t1 and the time point t2 may indicate the change in airway flow in the gas delivery section of the inspiration stage in a constant-flow ventilation mode, and specifically, the airway flow may be maintained at the preset airway flow setup value Fm. The dashed line may indicate the airway flow that the patient actually needs.

Figure 3:
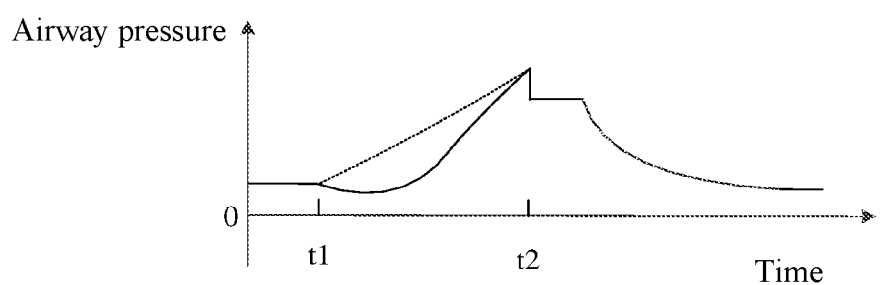
FIG. 3 is an exemplary schematic diagram of waveform of airway pressure versus time in the constant-flow ventilation mode provided by an embodiment of the disclosure.

FIG. 3 is an exemplary schematic diagram of waveform of airway pressure versus time in the constant-flow ventilation mode provided by an embodiment of the disclosure. As shown in FIG. 3, the gas delivery section of the inspiration stage may be from a time point t1 to a time point t2. The dashed line from the time point t1 to the time point t2 may indicate the change in airway pressure, specifically a monotonic rise, under normal situations in a constant-flow ventilation mode. The solid line from the time point t1 to the time point t2 may indicate a pressure drop of the airway pressure in the gas delivery section of the inspiration stage due to the insufficient airway flow of the ventilation apparatus, and the waveform of the airway pressure versus time specifically may have a spoon-shaped change, showing a non-monotonic rise. Moreover, the harder the patient inhales, more obvious the spoon-shaped change.

Specifically, in the embodiment of the disclosure, the step of identifying the improper setup of inspiratory pressure rise time by using the ventilation detection device according to the change trend of the respiratory parameter specifically may include: in a pressure ventilation mode, when the airway pressure is greater than a target value in an inspiratory pressure rise stage and the airway pressure fluctuates, determining that the inspiratory pressure rise time the ventilation apparatus may be too short; and/or in the pressure ventilation mode, when airway pressure has a pressure drop in the inspiratory pressure rise stage, determining that the inspiratory pressure rise time of the ventilation apparatus may be set too long.

It should be noted that in the pressure ventilation mode, the ventilation apparatus may be preset with an inspiratory pressure rise stage and a target value. Under normal situations, the ventilation apparatus may control the airway pressure to have a rapid rise to the target value in the inspiratory pressure rise stage and then be maintained at the target value for a period of time. However, when the inspiratory pressure rise stage is too short, it may exceed the patient's inspiratory response capacity, which may be indicated in that the airway pressure is greater than the target value at the end of the inspiratory pressure rise stage and fluctuates, that is, at the end of the inspiratory pressure rise stage, the airway pressure first instantaneously may exceed the target value and then fall back to the target value. When the inspiratory pressure rise stage is too long, it will fail to meet the patient's actual needs and will cause the patient to actively inhale and do extra work, which may be indicated by the pressure drop of the airway pressure in the inspiratory pressure rise stage.

Figure 4A:
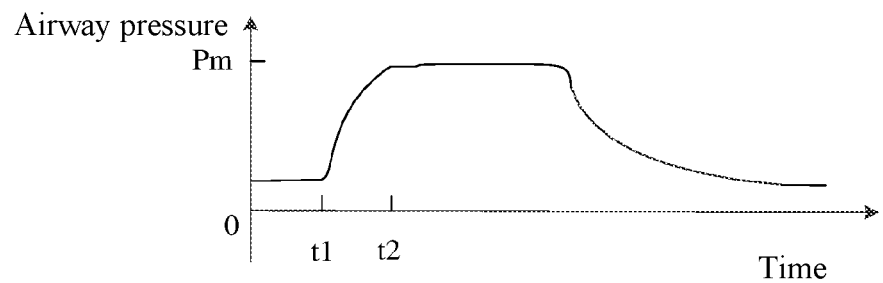
FIG. 4(a) is exemplary schematic diagram I of waveform of airway pressure versus time in a pressure ventilation mode provided by an embodiment of the disclosure.
Figure 4B:
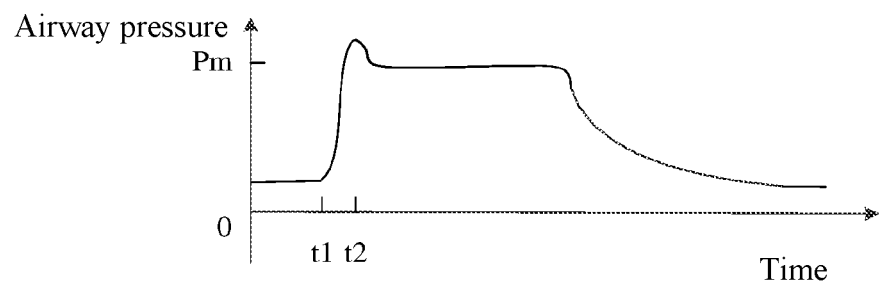
FIG. 4(b) is exemplary schematic diagram II of waveform of airway pressure versus time in the pressure ventilation mode provided by an embodiment of the disclosure.
Figure 4C:
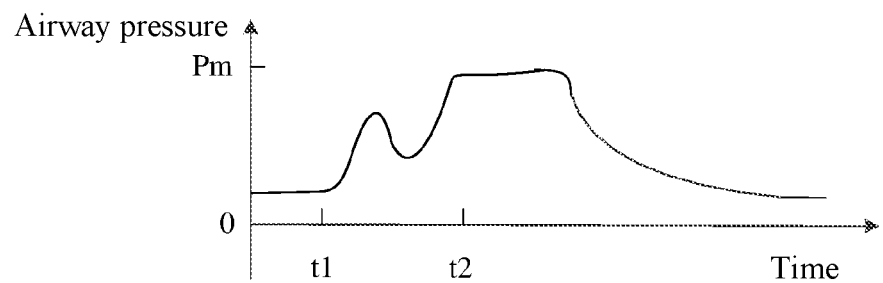
FIG. 4(c) is exemplary schematic diagram III of waveform of airway pressure versus time in the pressure ventilation mode provided by an embodiment of the disclosure.

FIG. 4(*a*) is exemplary schematic diagram I of waveform of airway pressure versus time in a pressure ventilation mode provided by an embodiment of the disclosure. As shown in FIG. 4(*a*), the inspiratory pressure rise stage may be from the time point t1 to the time point t2. Under normal situations, the airway pressure may have a rapid rise to a target value Pm in the period from the time point t1 to the time point t2 and may be then maintained at Pm, wherein the waveforms of airway pressure versus time may be smoothly connected.

FIG. 4(*b*) is exemplary schematic diagram II of waveform of airway pressure versus time in the pressure ventilation mode provided by an embodiment of the disclosure. As shown in FIG. 4(*b*), the inspiratory pressure rise stage may be from the time point t1 to the time point t2, in which the period from the time point t1 to the time point t2 may be shorter, and the airway pressure may rise too fast, as compared with the normal situation shown in FIG. 4(*a*), which may be indicated in that the airway pressure at the end of the inspiratory pressure rise stage may be greater than the preset airway pressure threshold Pm, and the airway pressure fluctuates.

FIG. 4(*c*) is exemplary schematic diagram III of waveform of airway pressure versus time in the pressure ventilation mode provided by an embodiment of the disclosure. As shown in FIG. 4(*c*), the inspiratory pressure rise stage may be from the time point t1 to the time point t2, in which the period from the period from the time point t1 to the time point t2 may be longer, and the airway pressure may rise too slowly, as compared with the normal situation shown in FIG. 4(*a*), which may be indicated by the pressure drop of the airway pressure in the inspiratory pressure rise stage and the spoon-shaped change of the waveform of the airway pressure versus time.

Specifically, in the embodiment of the disclosure, the step of identifying the improper setup of inspiratory duration by using the ventilation detection device according to the change trend of the respiratory parameter specifically may include: when the airway pressure has a rise or airway flow has an accelerated drop in an inspiration-to-expiration stage, determining that the inspiratory duration of the ventilation apparatus may be set too long; and when the airway pressure has a non-monotonic drop and/or airway flow has a non-monotonic rise in an expiration stage, determining that the inspiratory duration of the ventilation apparatus may be set too short.

It should be noted that, in the embodiment of the disclosure, the ventilation detection device can be preset with a drop threshold of the airway flow in the inspiration-to-expiration stage. When the airway flow in the inspiration-to-expiration stage is greater than the drop threshold during the actual mechanical ventilation, the ventilation detection device can determine that the inspiratory duration that is set for ventilation may be set too long. The specific drop threshold may be not limited according to the embodiment of the disclosure.

It should be noted that, under normal situations, the airway pressure and the airway flow may begin to gradually drop in the inspiration-to-expiration stage. However, when the inspiratory duration is set too long, the patient may have already begun to have an expiratory effort, but the ventilation apparatus still does not release gas, which may be indicated by the rise of airway pressure and the accelerated drop of airway flow in the inspiration-to-expiration stage. Under normal situations, in the expiration stage, the airway pressure of the ventilation apparatus may have a monotonic drop and the airway flow may have a monotonic rise. When the inspiratory duration is set too short, the ventilation apparatus may have begun to release gas, and the patient still may have an inspiratory effort, which may be indicated by the non-monotonic drop of the airway pressure and/or the non-monotonic rise of the airway flow in the expiration stage.

Figure 5A:
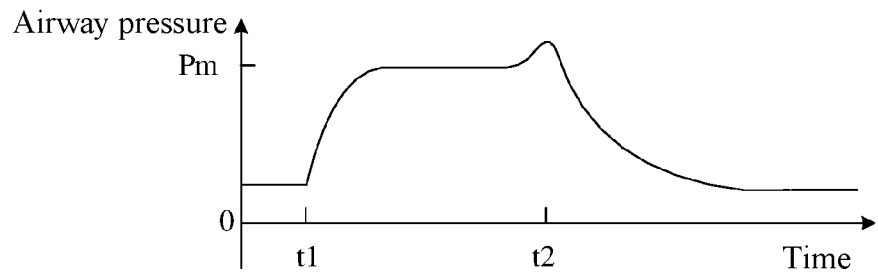
FIG. 5(a) is an exemplary schematic diagram of waveform of airway pressure versus time when an inspiratory duration is set too long provided by an embodiment of the disclosure.

FIG. 5(a) is an exemplary schematic diagram of waveform of airway pressure versus time when an inspiratory duration is set too long provided by an embodiment of the disclosure. As shown in FIG. 5(a), the inspiration stage may be from the time point t1 to the time point t2. When the period from the time point t1 to the time point t2 is set too long, in the inspiration-to-expiration stage, the airway pressure may have a rise, and the waveform of the airway pressure versus time may have an overshoot at the time point t2.

Figure 5B:
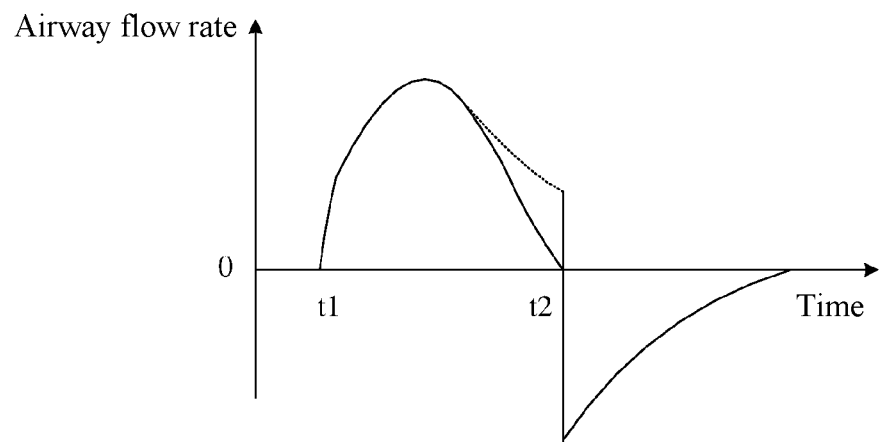
FIG. 5(b) is an exemplary schematic diagram of waveform of airway flow versus time when the inspiratory time is set too long provided by an embodiment of the disclosure.

FIG. 5(b) is an exemplary schematic diagram of waveform of airway flow versus time when the inspiratory time is set too long provided by an embodiment of the disclosure. Under normal situations, the inspiration-to-expiration stage may be the later stage of the period from the time point t1 to the time point t2, and the trend of the airway flow as shown by the dashed line in FIG. 5(b) gradually may decrease. However, when the inspiratory duration is set too long, the airway flow in the inspiration-to-expiration stage will have an accelerated drop, that is, the airway flow in the inspiration-to-expiration stage may be greater than the drop threshold, as shown by the solid line in FIG. 5(b).

Figure 6A:
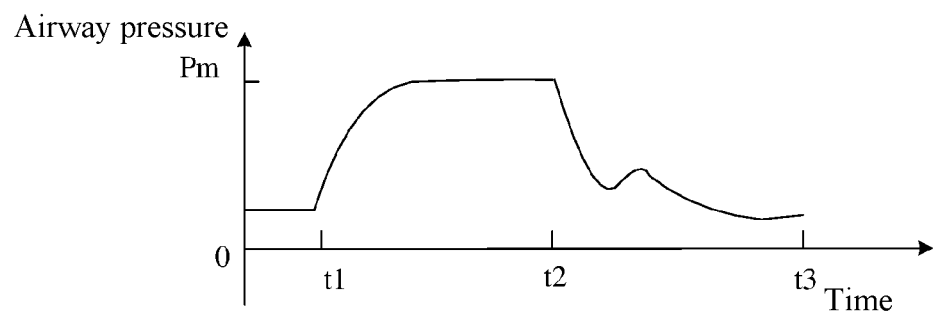
FIG. 6(a) is a schematic diagram of waveform of airway pressure versus time when the inspiratory duration is set too short provided by an embodiment of the disclosure.

FIG. 6(a) is a schematic diagram of waveform of airway pressure versus time when the inspiratory duration is set too short provided by an embodiment of the disclosure. As shown in FIG. 6(a), the inspiration stage may be from the time point t1 to the time point t2, and the expiration stage may be from the time point t2 to a time point t3. When the period from the time point t1 to the time point t2 is set too short, the airway pressure may be indicated to have a non-monotonic drop from the time point t2 to the time point t3.

Figure 6B:
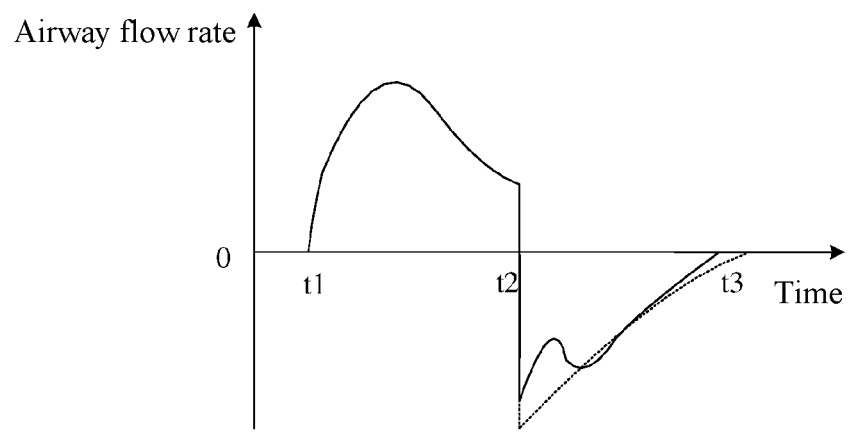
FIG. 6(b) is an exemplary schematic diagram of waveform of airway flow versus time when the inspiratory time is set too long provided by an embodiment of the disclosure.

FIG. 6(b) is an exemplary schematic diagram of waveform of airway flow versus time when the inspiratory time is set too short provided by an embodiment of the disclosure. As shown by the dashed line in FIG. 6(b), the inspiration stage may be from the time point t1 to the time point t2, and the expiration stage may be from the time point t2 to the time point t3. Under normal situations, the airway flow may have a monotonic drop from the time point t2 to the time point t3. However, when the inspiratory duration is set too short, the airway flow from the time point t2 to the time point t3 may have a non-monotonic rise, as shown by the solid line in FIG. 6(b).

Specifically, in the embodiment of the disclosure, the step of identifying the improper setup of expiratory duration by using the ventilation detection device according to the change trend of the respiratory parameter specifically may include: calculating the change in volume according to the airway flow rate; and when the airway flow is incapable of returning to a baseline but the volume is capable of returning to the baseline in an end expiration stage, determining that the expiratory duration of the ventilation apparatus may be set too short.

It should be noted that, in the embodiment of the disclosure, the ventilation detection device may detect the airway flow in real time, so the volume change can be calculated according to the change in the airway flow with time.

It should be noted that under normal situations, when the ventilation apparatus is switched to the expiration stage, a gas inlet end of the ventilation apparatus may be closed and an expiratory end may be opened. In principle, no matter how much gas the patient inhales, the gas can be exhaled from the expiratory end. However, when the expiratory duration is set too short, the patient cannot completely exhale gas, resulting in endogenous positive end-expiratory pressure ventilation, which will further affect inspiratory trigger, which may be indicated in that the airway flow in the end expiration stage is incapable of returning to the baseline and then the next respiratory cycle will start, but the volume is capable of returning to the baseline in the end expiration stage.

Figure 7A:
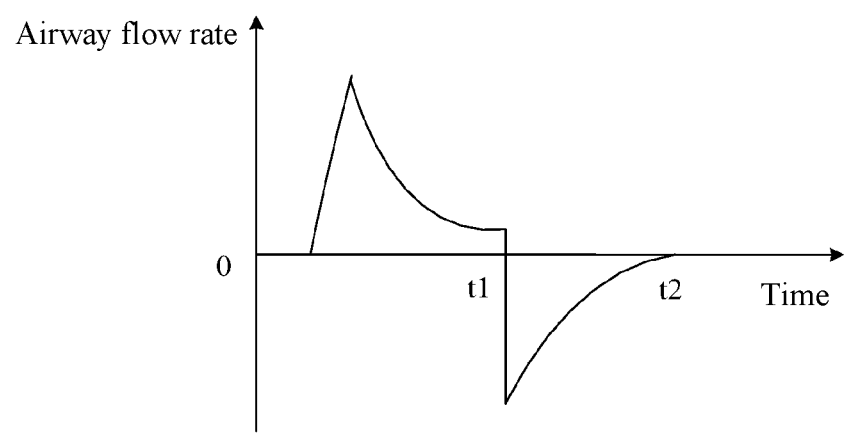
FIG. 7(a) is an exemplary schematic diagram of waveform of airway flow versus time during normal expiration provided by an embodiment of the disclosure.

FIG. 7(a) is an exemplary schematic diagram of waveform of airway flow versus time during normal expiration provided by an embodiment of the disclosure. As shown in FIG. 7(a), the expiration stage may be from the time point t1 to the time point t2, and the airway flow may return to the baseline at the time point t2, i.e., in the end expiration stage.

Figure 7B:
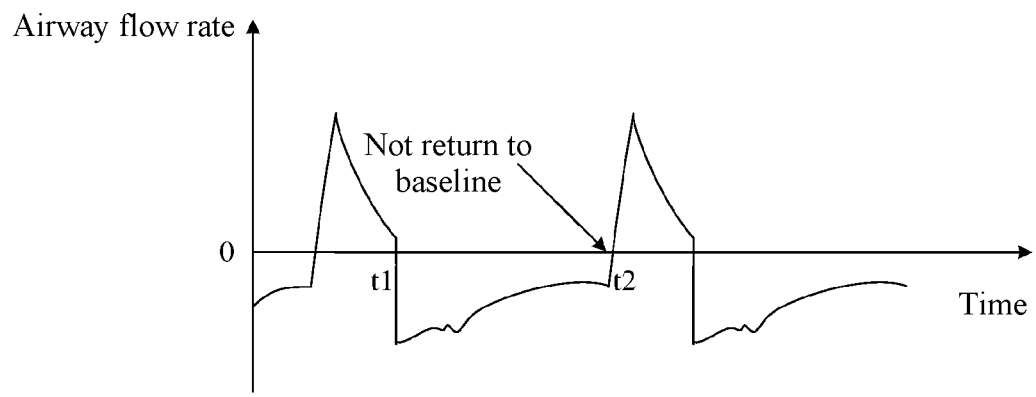
FIG. 7(b) is an exemplary schematic diagram of waveform of airway flow versus time when an expiratory duration is set too short provided by an embodiment of the disclosure.

FIG. 7(b) is an exemplary schematic diagram of waveform of airway flow versus time when an expiratory duration is set too short provided by an embodiment of the disclosure. As shown in FIG. 7(b), the expiration stage may be from the time point t1 to the time point t2. When the period from the time point t1 to the time point t2 is short, the airway flow may be incapable of returning to the baseline at the time point t2, i.e., in the end expiration stage.

Figure 7C:
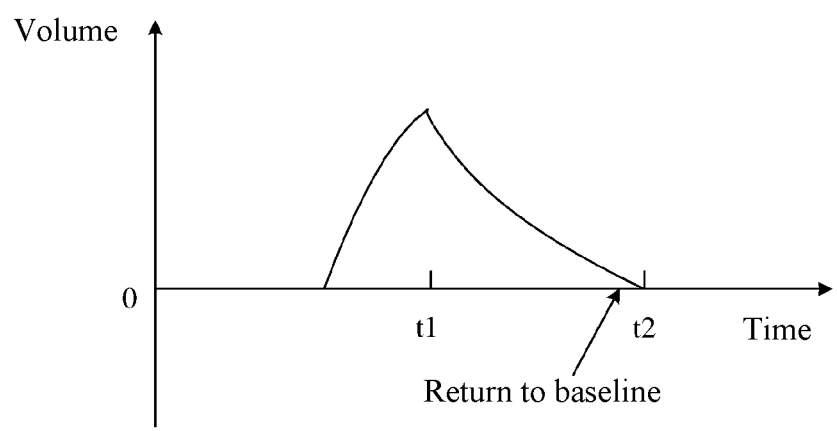
FIG. 7(c) is an exemplary schematic diagram of waveform of volume versus time when the expiratory duration is set too short provided by an embodiment of the disclosure.

FIG. 7(c) is an exemplary schematic diagram of waveform of volume versus time when expiratory duration is set too short provided by an embodiment of the disclosure. As shown in FIG. 7(c), the expiration stage may be from the time point t1 to the time point t2, and in the end expiration stage, i.e., at the time point t2, the airway flow may be incapable of returning to the baseline but the volume may be capable of returning to the baseline.

Specifically, in the embodiment of the disclosure, the step of identifying ventilation leakage by using the ventilation detection apparatus according to the change trend of the respiratory parameter specifically may include: calculating the change in volume according to the airway flow; and when the airway flow is incapable of returning to the baseline and the volume is incapable of returning to the baseline in the end expiration stage, determining that the ventilation apparatus may have a ventilation leakage.

It should be noted that when a pipeline of the ventilation apparatus leaks or a tracheal intubation balloon leaks, the ventilation leakage may have occurred, resulting in the volume of exhaled gas being less than that of the inhaled gas, which may be indicated in that the airway flow and volume may be incapable of returning to the baseline in the end expiration stage. The case where the airway flow is incapable of returning to the baseline in the end expiration stage may be similar to that shown in FIG. 7(b).

Figure 8:
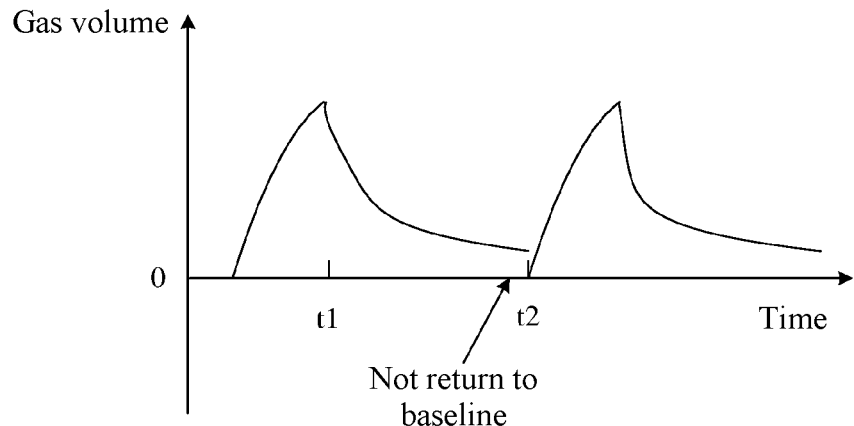
FIG. 8 is an exemplary schematic diagram of waveform of volume versus time during ventilation leakage provided by an embodiment of the disclosure.

FIG. 8 is an exemplary schematic diagram of waveform of volume versus time during ventilation leakage provided by an embodiment of the disclosure. As shown in FIG. 8, the expiration stage may be from the time point t1 to the time point t2, and when the ventilation leakage has occurred, the volume may be incapable of returning to the baseline at the time point t2, i.e., in the end expiration stage.

Figure 9:
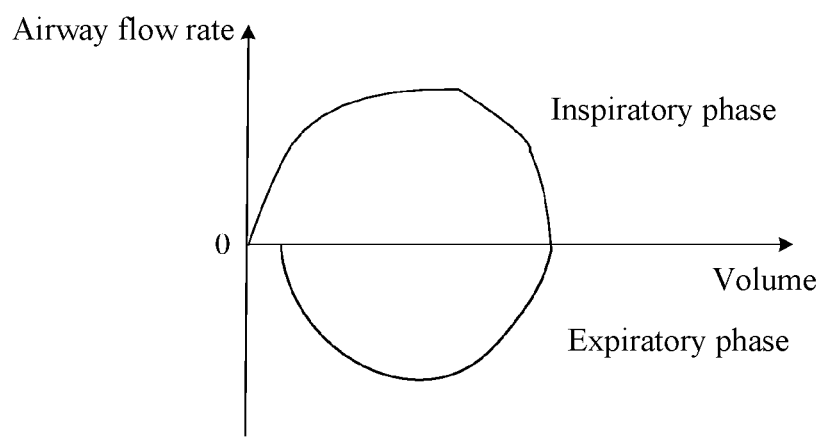
FIG. 9 is an exemplary loop of airway flow versus volume during ventilation leakage provided by an embodiment of the disclosure.

FIG. 9 is an exemplary loop of airway flow versus volume during ventilation leakage provided by an embodiment of the disclosure. As shown in FIG. 9, when the type of man-machine counteraction is ventilation leakage, the variation relationship between the volume and the airway flow during the entire mechanical ventilation can be indicated by this loop.

It should be noted that, in the embodiment of the disclosure, after identifying the type of man-machine counteraction according to the change trend of the respiratory parameter, the ventilation detection device can further output ventilation setup adjustment information of the ventilation apparatus according to the identified type of man-machine counteraction.

It should be noted that, in the embodiment of the disclosure, the ventilation setup adjustment information of the ventilation apparatus may be prompt information for making a relevant prompt or may be control information for making a relevant control for the ventilation setup. The ventilation setup adjustment information of the specific ventilation apparatus may be not limited according to the embodiment of the disclosure.

Exemplarily, in the embodiment of the disclosure, when the ventilation detection device identifies that the type of man-machine counteraction is the improper setup of inspiratory flow and the inspiratory flow of the ventilation apparatus is set insufficient, the ventilation setup adjustment information of the ventilation apparatus may be outputted as flashing of a target indicator light, such that after the target indicator light flashes, an operator who uses the ventilation apparatus to perform mechanical ventilation of the patient can obtain the type of man-machine counteraction and deal with it accordingly.

Exemplarily, in the embodiment of the disclosure, when the ventilation detection device identifies that the type of man-machine counteraction is improper setup of inspiratory pressure rise time and the inspiratory pressure rise time of the ventilation apparatus is set too short, the ventilation adjustment information of the ventilation apparatus may be outputted as follows: the inspiratory pressure rise time may be extended according to a preset time adjustment range, such that the ventilation apparatus can adjust the inspiratory pressure rise time according to the adjustment information.

It should be noted that, in the embodiment of the disclosure, after identifying the type of man-machine counteraction according to the change trend of the respiratory parameter, the ventilation detection device can further directly and autonomously adjust the ventilation parameter of the ventilation apparatus according to the identified type of man-machine counteraction.

Exemplarily, in the embodiment of the disclosure, after identifying that the type of man-machine counteraction is that the inspiratory pressure rise time is set too short or the inspiratory pressure rise time is set too long, the ventilation detection device automatically may adjust the inspiratory pressure rise time according to the preset time adjustment range, that is, the ventilation detection device can automatically shorten the inspiratory pressure rise time or extend the inspiratory pressure rise time according to the preset time adjustment range.

It should be noted that, in the embodiment of the disclosure, because the ventilation detection device or the ventilation apparatus cannot automatically make an adjustment for ventilation leakage, when the ventilation detection device identifies that the type of man-machine counteraction is ventilation leakage, the ventilation setup adjustment information of the ventilation apparatus that is output by using the ventilation detection device can only serve as prompt information, and no adjustment can be made.

Exemplarily, in the embodiment of the disclosure, the ventilation apparatus identifies that the type of man-machine counteraction may be ventilation leakage, and the ventilation setup adjustment information of the ventilation apparatus that is output by using the ventilation detection device may be giving an alarm prompt tone.

It should be noted that, in the embodiment of the disclosure, according to different types of the man-machine counteraction, there is different ventilation setup adjustment information of the ventilation apparatus. After identifying the type of man-machine counteraction, the ventilation detection device outputs the corresponding ventilation setup adjustment information of the ventilation apparatus.

An embodiment of the disclosure provides a ventilation detection method, including: monitoring respiratory parameters during the mechanical ventilation of a patient by using the ventilation apparatus, the respiratory parameters at least including one of airway pressure and airway flow rate; and using changes in the respiratory parameters to identify whether man-machine counteraction or ventilation leakage has occurred. That is to say, in the technical solution provided by the embodiment of the disclosure, it is possible to, during mechanical ventilation of a patient, identify man-machine counteraction or ventilation leakage according to specific changes in respiratory parameters and adjust the ventilation parameters or make a prompt according to the identified event to meet the patient's ventilation needs, thereby improving the therapeutic effect.

Embodiment II

Figure 10:
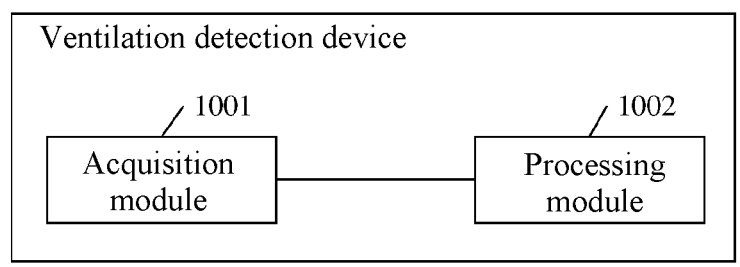
FIG. 10 is a schematic structural diagram of a ventilation detection device provided by an embodiment of the disclosure.

The embodiment of the disclosure provides a ventilation detection device. FIG. 10 is a schematic structural diagram of a ventilation detection device provided by an embodiment of the disclosure. As shown in FIG. 10, the ventilation detection device may include:

an acquisition unit 1001 may be configured to monitor respiratory parameters during mechanical ventilation of a patient by using a ventilation apparatus, the respiratory parameters may at least include one of airway pressure and airway flow rate; and a processing unit 1002 may be configured to use changes in the respiratory parameters to identify whether man-machine counteraction or ventilation leakage has occurred.

Optionally, the processing unit 1002 may be configured to analyze a change trend of the respiratory parameter; and identify whether man-machine counteraction or ventilation leakage has occurred according to the change trend of the respiratory parameter.

Optionally, the processing unit 1002 may be configured to, after identifying that man-machine counteraction has occurred according to the change trend of the respiratory parameter, identify the type of man-machine counteraction according to the change trend of the respiratory parameter.

Optionally, the type of man-machine counteraction may include one or more of improper setup of inspiratory flow, improper setup of inspiratory pressure rise time, improper setup of inspiratory duration, and improper setup of expiratory duration.

Optionally, the step of identifying the improper setup of inspiratory flow by using the processing unit 1002 according to the change trend of the respiratory parameter specifically may include:
  in a constant-flow ventilation mode, when pressure drop has occurred in a gas delivery section in an inspiration stage, determining that the inspiratory flow of the ventilation apparatus may be set insufficient.

Optionally, the step of identifying the improper setup of inspiratory pressure rise time by using the processing unit 1002 according to the change trend of the respiratory parameter specifically may include:
  in a pressure ventilation mode, when the airway pressure is greater than a target value at the end of an inspiratory pressure rise stage and the airway pressure fluctuates, determining that the inspiratory pressure rise time of the ventilation apparatus may be set too short; and/or
  in the pressure ventilation mode, when the airway pressure has a pressure drop in the inspiratory pressure rise stage, determining that the inspiratory pressure rise time of the ventilation apparatus may be set too long.

Optionally, the step of identifying the improper setup of inspiratory duration by using the processing unit 1002 according to the change trend of the respiratory parameter specifically may include:
  when the airway pressure has a rise or the airway flow has an accelerated drop in an inspiration-to-expiration stage, determining that the inspiratory duration of the ventilation apparatus may be set too long; and
  when the airway pressure has a non-monotonic drop and/or the airway flow has a non-monotonic rise in an expiration stage, determining that the inspiratory duration of the ventilation apparatus may be set too short.

Optionally, the step of identifying the improper setup of expiratory duration by using the processing unit 1002 according to the change trend of the respiratory parameter specifically may include:
  calculating the change in volume according to the airway flow; and
  when the airway flow is incapable of returning to a baseline and the volume is capable of returning to the baseline in an end expiration stage, determining that the expiratory duration of the ventilation apparatus may be set too short.

Optionally, the step of identifying the ventilation leakage by using the processing unit 1002 according to the change trend of the respiratory parameter specifically may include:
  calculating the change in volume according to the airway flow rate; and when the airway flow is incapable of returning to the baseline and the volume is incapable of returning to the baseline in the end expiration stage, determining that the ventilation apparatus may have a ventilation leakage.

Optionally, after the step of identifying the type of man-machine counteraction according to the change trend of the respiratory parameter, the processing unit 1002 may output ventilation setup adjustment information of the ventilation apparatus according to the identified type of man-machine counteraction.

Optionally, after the step of identifying the type of man-machine counteraction according to the change trend of the respiratory parameter, the processing unit 1002 may adjust the ventilation parameter of the ventilation apparatus according to the identified type of man-machine counteraction.

An embodiment of the disclosure may provide a ventilation detection device, including: monitoring respiratory parameters during the mechanical ventilation of a patient by using the ventilation apparatus, the respiratory parameters at least including one of airway pressure and airway flow; and using changes in the respiratory parameters to identify whether man-machine counteraction or ventilation leakage has occurred. That is to say, in the ventilation detection device provided by the embodiment of the disclosure, it is possible to, during mechanical ventilation of a patient, identify man-machine counteraction or ventilation leakage according to specific changes in respiratory parameters and adjust the ventilation parameters or make a prompt according to the identified event to meet the patient's ventilation needs, thereby improving the therapeutic effect.

Figure 11:
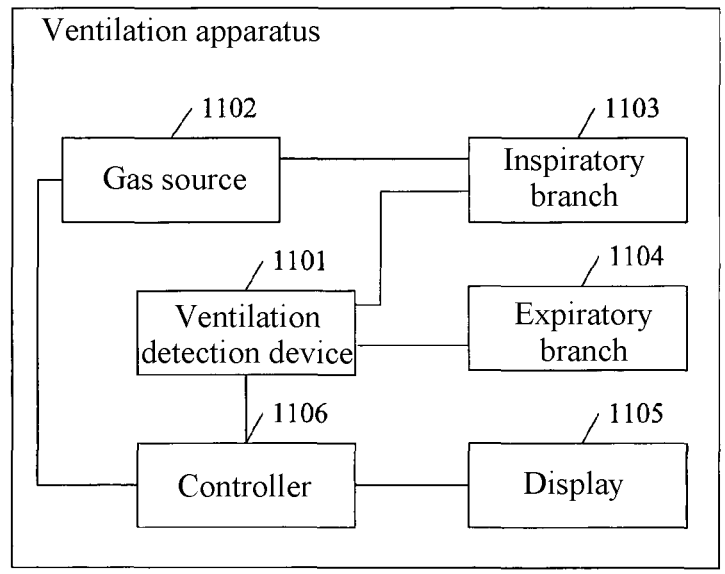
FIG. 11 is schematic structural diagram I of a ventilation apparatus provided by an embodiment of the disclosure.

An embodiment of the disclosure further provides a ventilation apparatus. FIG. 11 is schematic structural diagram I of a ventilation apparatus provided by an embodiment of the disclosure. As shown in FIG. 11, the ventilation apparatus may include the ventilation detection device 1101 mentioned above, and further include: a gas source 1102, an inspiratory branch 1103, an expiratory branch 1104, a display 1105, and a controller 1106; wherein the gas source 1102 may provide gas during mechanical ventilation;
  the inspiratory branch 1103 may be connected to the gas source 1102, and
  provide an inspiratory path during the mechanical ventilation;
  the expiratory branch 1104 may provide an expiratory path during the mechanical ventilation;
  the ventilation detection device 1101 may be connected to the inspiratory branch 1103, the expiratory branch 1104 and the controller 1106;
  the ventilation detection device 1101 may perform ventilation detection during the mechanical ventilation;
  the controller 1106 may be further connected to the gas source 1102, and control the process of the mechanical ventilation; and
  the display 1105 may be connected to the controller 1106, and display a respiratory waveform during the mechanical ventilation.

Figure 12:
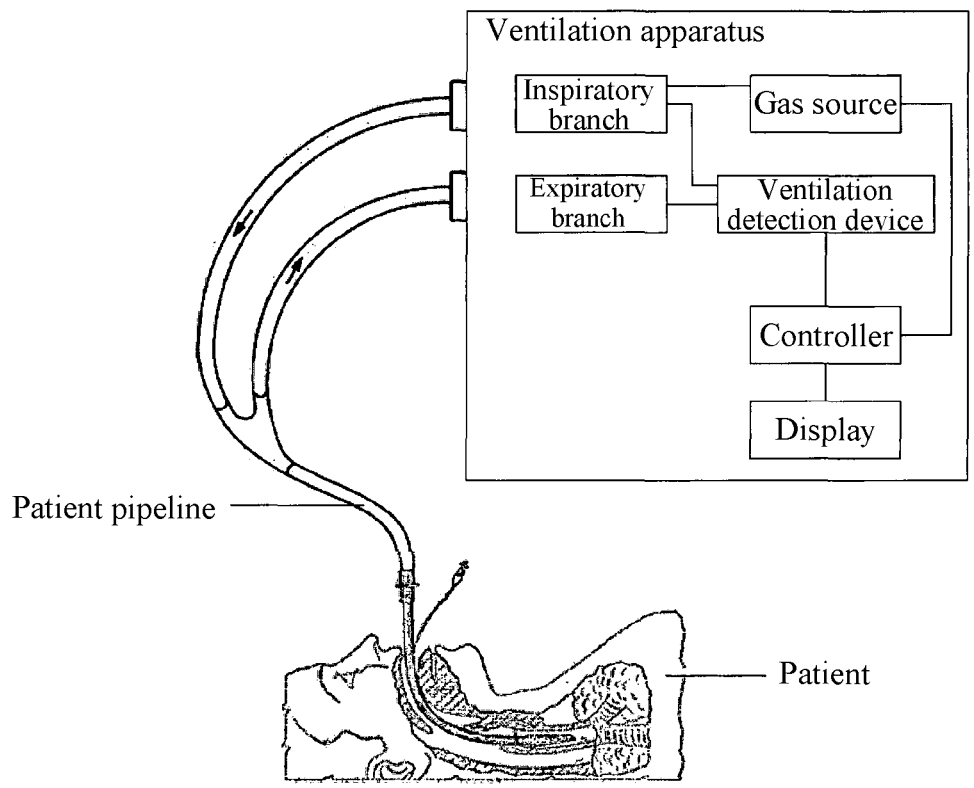
FIG. 12 is schematic structural diagram II of a ventilation apparatus provided by an embodiment of the disclosure.

FIG. 12 is schematic structural diagram II of a ventilation apparatus provided by an embodiment of the disclosure. As shown in FIG. 12, a patient can be connected with a ventilation apparatus through a patient pipeline to implement mechanical ventilation, wherein the ventilation apparatus includes the ventilation detection device.

The embodiment of the disclosure provides a computer-readable storage medium, wherein the computer-readable storage medium stores a ventilation detection program, and the ventilation detection program is executable by a processor to implement the above ventilation detection method. A computer-readable storage medium may be a volatile memory, such as a Random-Access Memory (RAM); or a non-volatile memory, such as a Read-Only Memory (ROM), a flash memory, a Hard Disk Drive (HDD) or a Solid-State Drive (SSD); or a respective apparatus including one or any combination of the above memories, such as a mobile phone, a computer, a tablet apparatus, and a personal digital assistant.

Those skilled in the art should understand that the embodiments of the disclosure may be provided as a method, a system, or a computer program product. Therefore, the disclosure may use the form of a hardware embodiment, a software embodiment, or a software and hardware combined embodiment. Moreover, the disclosure may use a form of a computer program product that is implemented on one or more computer-usable storage media (including but not limited to a disk memory and an optical memory, etc.) that include computer-usable program codes.

The disclosure is described with reference to flow charts and/or block diagrams of methods, devices (systems), and computer program products according to embodiments of the disclosure. It should be understood that each flow and/or block in the flow charts and/or block diagrams, and combinations of flows and/or blocks in the flow charts and/or block diagrams can be implemented by computer program instructions. These computer program instructions may be provided to a processor of a general-purpose computer, a special-purpose computer, an embedded processor, or another programmable signal processing device to produce a machine, such that the instructions executed by the processor of the computer or another programmable signal processing device produce an apparatus for implementing functions specified in one or more flows in the flow chart and/or one or more blocks in the block diagram.

These computer program instructions may also be stored in a computer-readable memory that can direct a computer or another programmable signal processing device to operate in a specific manner, such that the instructions stored in the computer-readable memory produce an article of manufacture including an instruction apparatus, and the instruction apparatus implements functions specified in one or more flows of the flow chart and/or one or more blocks of the block diagram.

These computer program instructions can also be loaded onto a computer or another programmable signal processing device, such that a series of operation steps are executed on the computer or another programmable device to perform computer-implemented processing, and thus the instructions executed on the computer or another programmable device provide steps for implementing functions specified in one or more flows of the flow chart and/or one or more blocks of the block diagram.

The forgoing description is only preferred embodiments of the disclosure, and is not intended to limit the scope of protection of the disclosure.

INDUSTRIAL APPLICABILITY

In the technical solutions of the embodiment of the disclosure, the ventilation detection device is configured for monitoring respiratory parameters during the mechanical ventilation of a patient by using the ventilation apparatus, the respiratory parameters at least including one of airway pressure and airway flow; and using changes in the respiratory parameters to identify whether man-machine counteraction or ventilation leakage has occurred. That is to say, in the technical solution provided by the embodiment of the disclosure, it is possible to, during mechanical ventilation of a patient, identify man-machine counteraction or ventilation leakage according to specific changes in respiratory parameters and adjust the ventilation parameters or make a prompt according to the identified event to meet the patient's ventilation needs, thereby improving the therapeutic effect.

The invention claimed is:

1. A ventilation detection method for a ventilation apparatus comprising an inspiratory branch, an expiratory branch and a controller, the method comprising:

monitoring, by a ventilation detection device connected to the inspiratory branch, the expiratory branch and the controller of the ventilation apparatus, a respiratory parameter during mechanical ventilation of a patient by using the ventilation apparatus, the respiratory parameter comprising an airway flow; and using a change of the respiratory parameter to identify whether a man-machine counteraction has occurred and identify a type of the man-machine counteraction, wherein when the type of the man-machine counteraction is an improper setup of expiratory duration, using the change of the respiratory parameter to identify whether the man-machine counteraction has occurred, comprises:

calculating, by the ventilation detection device, a change of a volume according to the airway flow; and when the airway flow is incapable of returning to a baseline, but the volume is capable of returning to a baseline at an end of an expiration stage, determining, by the ventilation detection device, that the expiratory duration is set shorter than expiratory duration of the patient; and adjusting a ventilation parameter of the ventilation apparatus according to the identified type of the man-machine counteraction.

2. The ventilation detection method of claim 1, wherein using a change of the respiratory parameter to identify whether the man-machine counteraction has occurred comprises:

analyzing a change trend of the respiratory parameter; and identifying whether the man-machine counteraction has occurred according to the change trend of the respiratory parameter.

3. The ventilation detection method of claim 2, further comprising:

identifying the type of the man-machine counteraction according to the change trend of the respiratory parameter.

4. The ventilation detection method of claim 3, wherein the type of the man-machine counteraction comprises one or more of an improper setup of inspiratory flow, an improper setup of inspiratory pressure rise time, an improper setup of inspiratory duration, or the improper setup of expiratory duration.

5. The ventilation detection method of claim 4, wherein the respiratory parameter further comprises an airway pressure, wherein when the type of the man-machine counteraction further comprises the improper setup of inspiratory flow, identifying, a type of the man-machine counteraction according to the change trend of the respiratory parameter further comprises:

in a constant-flow ventilation mode, when a pressure drop has occurred in a gas delivery section in an inspiration stage, determining that a preset airway flow in the gas delivery section of the inspiration stage is set insufficiently.

6. The ventilation detection method of claim 4, wherein the respiratory parameter further comprises an airway pressure, wherein when the type of the man-machine counteraction further comprises the improper setup of inspiratory pressure rise time, identifying a type of the man-machine counteraction according to the change trend of the respiratory parameter further comprises:

in a pressure ventilation mode, when the airway pressure is greater than a target value at an end of an inspiratory pressure rise stage and the airway pressure fluctuates, determining that the inspiratory pressure rise time of the ventilation apparatus is set too short; or in a pressure ventilation mode, when the airway pressure has a pressure drop in an inspiratory pressure rise stage, determining that the inspiratory pressure rise time of the ventilation apparatus is set too long.

7. The ventilation detection method of claim 4, wherein the respiratory parameter further comprises an airway pressure, wherein when the type of the man-machine counteraction further comprises the improper setup of inspiratory duration, identifying a type of the man-machine counteraction according to the change trend of the respiratory parameter further comprises:

when the airway pressure has a rise or the airway flow has an accelerated drop in an inspiration-to-expiration stage, determining that the inspiratory duration is set longer than inspiratory duration of the patient; and when the airway pressure has a non-monotonic drop or the airway flow has a non-monotonic rise in an expiration stage, determining that the inspiratory duration is set shorter than the inspiratory duration of the patient.

8. The ventilation detection method of claim 3, further comprising calculating a change of a volume according to the airway flow; and when the airway flow is incapable of returning to a baseline and the volume is also incapable of returning to a baseline at an end of an expiration stage, determining that the ventilation apparatus has a ventilation leakage.

9. The ventilation detection method of claim 3, further comprising:

outputting ventilation setup adjustment information of the ventilation apparatus according to the identified type of the man-machine counteraction.

10. A ventilation detection device, comprising:

an acquisition unit, connected to an inspiratory branch, an expiratory branch and a controller of a ventilation apparatus, configured to monitor a respiratory parameter during a mechanical ventilation of a patient by using a ventilation apparatus, the respiratory parameter comprising an airway flow; and a processing unit configured to use a change of the respiratory parameter to identify whether a man-machine counteraction has occurred and identify a type of the man-machine counteraction, wherein when a type of the man-machine counteraction is an improper setup of expiratory duration, using the change of the respiratory parameter to identify whether the improper setup of expiratory duration has occurred comprises:

calculating a change of a volume according to the airway flow; and when the airway flow is incapable of returning to a baseline, but the volume is capable of returning to a baseline at an end of an expiration stage, determining that the expiratory duration is set shorter than expiratory duration of the patient, wherein the processing unit is further configured to adjust a ventilation parameter of the ventilation apparatus according to the identified type of man-machine counteraction.

11. The ventilation detection device of claim 10, wherein the processing unit is further configured to:

analyze a change trend of the respiratory parameter; and identify whether the man-machine counteraction has occurred according to the change trend of the respiratory parameter.

12. The ventilation detection device of claim 11, wherein the processing unit is configured to identify the type of the man-machine counteraction according to the change trend of the respiratory parameter.

13. The ventilation detection device of claim 12, wherein the type of man-machine counteraction comprises one or more of an improper setup of inspiratory flow rate, an improper setup of inspiratory pressure rise time, an improper setup of inspiratory duration, or the improper setup of expiratory duration.

14. The ventilation detection device of claim 13, wherein the respiratory parameter further comprises an airway pressure, wherein when the type of the man-machine counteraction further comprises the improper setup of inspiratory flow, to identify a type of the man-machine counteraction according to the change trend of the respiratory parameter, the processing unit is further configured to:

in a constant-flow ventilation mode, when a pressure drop has occurred in a gas delivery section in an inspiration stage, determine that a preset airway flow in the gas delivery section of the inspiration stage is set insufficient.

15. The ventilation detection device of claim 13, wherein the respiratory parameter further comprises an airway pressure, wherein when the type of the man-machine counteraction further comprises the improper setup of inspiratory pressure rise time, to identify a type of the man-machine counteraction according to the change trend of the respiratory parameter, the processing unit is further configured to:

in a pressure ventilation mode, when the airway pressure is greater than a target value at an end of an inspiratory pressure rise stage and the airway pressure fluctuates, determine that the inspiratory pressure rise time of the ventilation apparatus is set too short; or in the pressure ventilation mode, when the airway pressure has a pressure drop in the inspiratory pressure rise stage, determine that the inspiratory pressure rise time of the ventilation apparatus is set too long.

16. The ventilation detection device of claim 13, wherein the respiratory parameter further comprises an airway pressure, wherein when the type of the man-machine counteraction further comprises the improper setup of inspiratory duration, identifying a type of the man-machine counteraction according to the change trend of the respiratory parameter, the processing unit is further configured to:

when the airway pressure has a rise or the airway flow has an accelerated drop in an inspiration-to-expiration stage, determine that the inspiratory duration is set longer than inspiratory duration of the patient; and when the airway pressure has a non-monotonic drop or the airway flow has a non-monotonic rise in an expiration stage, determine that the inspiratory duration is set shorter than the inspiratory duration of the patient.

17. The ventilation detection device of claim 12, wherein the processing unit is further configured to:

calculate a change of a volume according to the airway flow rate; and when the airway flow is incapable of returning to the baseline and the volume is incapable of returning to the baseline in an end of an expiration stage, determine that the ventilation apparatus has a ventilation leakage.

18. The ventilation detection device of claim 12, wherein the processing unit is further configured to output a ventilation setup adjustment information of the ventilation apparatus according to the identified type of man-machine counteraction.

19. A ventilation apparatus comprising a ventilation detection device, a gas source, an inspiratory branch, an expiratory branch, a display, and a controller, wherein
the gas source provides a gas during a mechanical ventilation;
the inspiratory branch is connected to the gas source, and provides an inspiratory path during the mechanical ventilation;
the expiratory branch provides an expiratory path during the mechanical ventilation;
the controller is further connected to the gas source, and controls the mechanical ventilation;
the display is connected to the controller, and displays a respiratory waveform during the mechanical ventilation; and
the ventilation detection device is used for performing a ventilation detection during the mechanical ventilation, and is connected to the inspiratory branch, the expiratory branch, and the controller respectively, wherein the ventilation detection device comprises:
an acquisition unit, connected to an inspiratory branch, an expiratory branch and a controller of a ventilation apparatus, configured to monitor a respiratory parameter during the mechanical ventilation of a patient, the respiratory parameter comprising at least one of an airway pressure of an airway flow; and
a processing unit configured to use a change of the respiratory parameter to identify whether a man-machine counteraction has occurred and identify a type of the man-machine counteraction,
wherein when a type of the man-machine counteraction is an improper setup of expiratory duration, the processing unit is further configured to:
calculate a change of a volume according to the airway flow; and
when the airway flow is incapable of returning to a baseline, but the volume is capable of returning to a baseline at an end of an expiration stage, determine that the expiratory duration is set shorter than expiratory duration of the patient,
wherein the processing unit is further configured to adjust a ventilation parameter of the ventilation apparatus according to the identified type of man-machine counteraction.

* * * * *